United States Patent [19]

Alfred et al.

[11] Patent Number: 4,748,029
[45] Date of Patent: May 31, 1988

[54] METHOD FOR CONTROLLING THE FLOW OF A PRODUCT ONTO A CONVEYOR BELT

[75] Inventors: Per A. Alfred; Karl C. Dahlberg, both of Helsingborg, Sweden

[73] Assignee: Frigoscandia Contracting AB, Helsingborg, Sweden

[21] Appl. No.: 876,702

[22] Filed: Jun. 19, 1986

[30] Foreign Application Priority Data

Jun. 26, 1985 [SE] Sweden ............................. 8503158

[51] Int. Cl.$^4$ ............................................. F25D 25/04
[52] U.S. Cl. ........................................ 426/231; 62/63; 62/345; 239/11; 239/63
[58] Field of Search .................... 426/231, 524; 62/63, 62/64, 373, 374, 375, 380, 345; 239/101, 63, 11

[56] References Cited

U.S. PATENT DOCUMENTS

| | | | |
|---|---|---|---|
| 3,253,420 | 5/1966 | George | 426/524 |
| 3,628,726 | 12/1971 | Johnson | 239/101 |
| 3,776,460 | 12/1973 | Fichter | 239/101 |
| 4,064,295 | 12/1977 | Singer | 239/11 |

FOREIGN PATENT DOCUMENTS 0061922 10/1982 European Pat. Off. ............. 239/63

Primary Examiner—Steve Alvo
Attorney, Agent, or Firm—Browdy and Neimark

[57] ABSTRACT

In a method for controlling the flow of a pumpable food product into an apparatus comprising a conveyor belt to which the product is applied and converted from liquid to solid phase, the angle of spreading of the product applied to the conveyor belt is sensed and compared with a predetermined angle of spreading. The flow of product is so controlled that the difference between these angles is reduced. An apparatus for carrying out the method includes a horizontal belt conveyor having a conveyor belt for treating a web or mat of a pumpable product which is applied to the belt and spread over its entire width. A detector senses the angle of spreading of the product on the belt, and a control unit controls the flow of product applied such that the angle of spreading will have a predetermined value.

3 Claims, 1 Drawing Sheet

METHOD FOR CONTROLLING THE FLOW OF A PRODUCT ONTO A CONVEYOR BELT

BACKGROUND OF THE INVENTION

The present invention relates to a method for controlling the flow of a pumpable product into a food treating apparatus comprising a conveyor belt on which the product is spread in order to be converted from liquid to solid phase. The invention also relates to an apparatus for carrying out the method, the apparatus comprising a substantially horizontal belt conveyor having a conveyor belt for treating a web or mat of a pumpable product, which is applied to the belt and spread over the entire width thereof, in such a manner that the product is solidified.

Apparatuses of this kind are previously known and are advantageously used, for instance, for freezing liquid or semi-liquid products, which should be formed into pellets readily portionable in the frozen state. Examples of such products are spinach, cream and sauces.

When variations appear in the speed of the conveyor belt in such an apparatus, the flow of product into the apparatus must be adjusted to maintain the correct filling degree therein. Because of e.g. the delays inherent in such a system, this adjustment has been found to entail great problems.

SUMMARY OF THE INVENTION

The object of the present invention therefore is to provide a method and an apparatus of the types which are mentioned in the introduction to this specification and which overcome the above-indicated difficulties.

According to the invention, these objects are achieved by a method wherein the angle of spreading of the product applied to the conveyor belt is sensed and compared with a predetermined angle of spreading, and wherein said flow is so controlled that the difference between said two angles is reduced.

Further, the apparatus according to the invention comprises a detector for sensing the angle of spreading of the product applied to the belt, and a control unit for adjusting the supplied product flow in such a manner that said angle of spreading attains a predetermined value.

BRIEF DESCRIPTION OF THE DRAWINGS

One embodiment of a freezer according to the present invention will be described in greater detail hereinbelow with reference to the accompanying drawing in which.

DESCRIPTION OF THE PREFERRED EMBODIMENT

Figure 1:
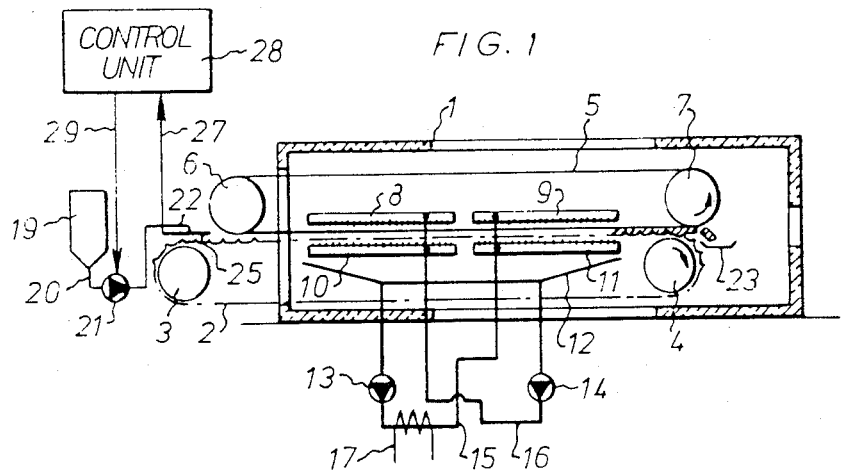
FIG. 1 is a schematic side view of a freezer according to one embodiment of the invention.

The freezer shown in FIG. 1 has an elongate freezing chamber 1. A lower conveyor belt 2 extends substantially horizontally from a return pulley 3 outside one end of the chamber 1, into the chamber 1 and through it to a return pulley 4 adjacent the opposite end of the chamber 1 and back to the return pulley 3. An upper conveyor belt 5 extends from a return pulley 6, also located outside but closer to said one end of the chamber 1, into the chamber 1 and through it to a return pulley 7 disposed immediately above or slightly beyond the return pulley 4, and back to the return pulley 6.

The belt 2 has depressions at least on its outwardly facing side and is preferably corrugated with corrugations extending transversely of the longitudinal direction of the belt 2. The belt 5, where its path of travel is common to that of the belt 2, is spaced a certain distance from the belt 2 and preferably consists of a planar and smooth belt. Both the belt 2 and the belt 5 may consist of stainless steel.

Within the chamber 1, a freezing zone is provided in that several sets 8-11 of spray nozzles for a refrigerating medium, for instance glycol brine, are provided on the sides of the belts 2, 5 facing away from each other within the common extent of the belts. Below the lower sets of nozzles 10, 11, there is provided a collecting trough 12 having outlets to two pumps 13, 14 which by conduits 15, 16 feed the refrigerating medium to the nozzles of the sets 9, 11, and 8, 10, respectively. The conduit 15 from the pump 13 passes a cooler 17 for the refrigerating medium. Thus, there is a more vigorous cooling effect from nozzle sets 9, 11.

From the region of the return pulleys 3, 6 and along the freezing zone, there extend side walls 18 (shown in FIG. 3 only) which preferably consist of rubber strips which are fixedly mounted at the side edges of the belt 2 and form a sealing connection against the adjacent side edges of the belt 5, whereby a transversely closed channel is formed before and through the freezing zone.

A tank 19 for the product to be frozen in the freezer communicates by a conduit 20 and a pump 21 connected therein, with a spreader nozzle 22 centrally disposed above the belt 2 at its exposed, substantially horizontal portion in front of the return pulley 6.

The freezer described above operates in the following way. The pumpable liquid or semi-liquid product to be frozen is discharged from the spreader nozzle 22 and spreads in a V-shape as it flows across the belt 2 towards the side edges thereof, provided the belt 2 is moving into the chamber 1. The belt speed and the temperature and flow rate of the refrigerating medium are adjusted in such a manner that the product is frozen so as to form a coherent web or mat which is discharged from between the return pulleys 4, 7 at a predetermined temperature.

When emerging from between the pulleys 4, 7, the frozen product mat can be cut by suitable means (e.g. a saw or knife) into smaller pieces or pellets which are conveyed, e.g. to a packaging unit, by means of a conveyor 23 travelling transversely of the belts 2, 5.

The adjustment of the above-mentioned parameters, i.e. belt speed and temperature and flow rate of the refrigerating medium, often differs from one product to another. A modification of any one of these parameters during operation may also necessitate a modification of one or both of the other two. This necessitates an adjusted flow of the product from the spreader 22, such that the product will accurately fill the space between the belts 2 and 5, which is of essential importance for obtaining the desired product mat. The supply of the product must be carried out so accurately that the product level will not exceed the edges of the rubber strips 18 of the belt 2.

According to the present invention, use is made of the fact that for a pumpable food product flow from the spreader nozzle 22 that is adjusted to the selected belt speed for obtaining the desired temperature of the frozen product mat, the angle of spreading A of the food product as it flows on the belt 2 (see FIG. 3) has been found to have an empirically predeterminable value which, in addition to the belt speed, is also dependent upon the viscosity of the food product. By sensing the angle of spreading A of the product on the belt 2 and adjusting the feed of the product by means of the pump 21 in dependence upon the sensed angle of spreading A, the flow of product into the freezer can be continuously maintained on a correct level. In order to achieve optimal adjustment, the spreader nozzle 22 is adjustable in the longitudinal direction of the belt 2. Thus, the product flow can be caused, at a desired angle of spreading, to encounter the rubber strips 18 just before the belt 5 makes contact with the rubber strips 18.

Figure 2:
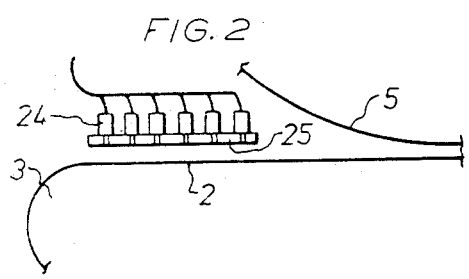
FIG. 2, on a larger scale, shows the infeed end of the freezer in FIG. 1.
Figure 3:
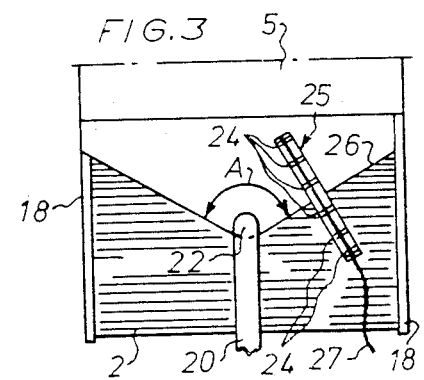
FIG. 3 is a top plan view corresponding to FIG. 2.

A detector device for carrying out the adjustment is shown in greater detail in FIGS. 2 and 3. The detector device comprises six photodetectors 24 which are mounted on an arm 25 positioned above the belt 2 adjacent the spreader nozzle 22 substantially transversely of one spreading front 26 of the product on the belt 2. The photodetectors 24 are mounted at varying distances from the centre of the arm 25, which centre is positioned straight above and in alignment with the predetermined position of the spreading front 26 of the product. Thus, by means of the photodetectors 24, the position of the spreading front 26 can be established as one of seven possible positions. For effecting the adjustment of the pump 21 and the flow therethrough, the photodetectors 24 are connected, more precisely, by a line 27 to a control unit 28 which in turn controls the pump 21 by a line 29, as shown in FIG. 1. The adjustment of the pump 21 may then suitably be so effected that the flow through the pump is modified stepwise and increasingly the farther away from the central position between the central photodetectors 24 the spreading front 26 of the product is located.

In the above-described embodiment, the accuracy of the adjustment is determined both by the number of photodetectors 24 and by the mutual spacing thereof. Further, it is assumed that the spreading configuration is symmetrical about the centre line of the belt 2 such that the adjustment can be effected on the basis of the position of one spreading front 26 only.

Figure 4:
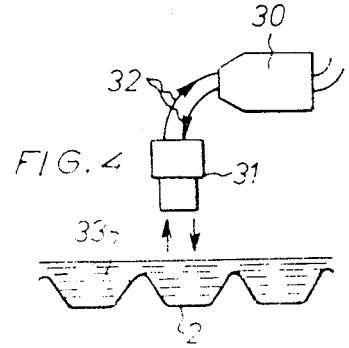
FIGS. 4, 5 and 6 illustrate an embodiment of a detector used in the freezer according to the invention, and the mode of operation thereof.
Figure 5:
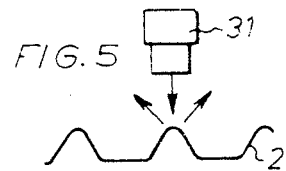
Figure 6:
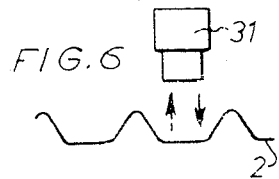

The mode of operation of the photodetectors 24 appears from FIGS. 4, 5 and 6. As shown in FIG. 4, a photodetector 24 may consist of a detector unit 30 and a lens unit 31 which are connected to optical fibre conductors 32. In FIG. 4, there is shown a product layer 33 distributed across the belt 2, the light emitted by the lens unit 31 being reflected towards the photodetector 24 without any major variation. The signal then emitted by the detector unit 30 to the control unit 28 therefore has a substantially constant level.

If, on the other hand, there is no product layer immediately underneath one of the photodetectors 24, the light emitted from the lens unit 31 thereof will be reflected in a varying degree because of the corrugation of the belt 2. This is illustrated in FIGS. 5 and 6 for two longitudinal positions of the belt 2 relative to a lens unit 31. In this case, the control unit 28 will receive a signal having an amplitude varying according to the corrugations on the belt 2.

By determining the type of signal emitted by the different photodetectors 24, the control unit 28 can thus decide the position of the spreading front 26 on the belt 2 and control the pump 21 in a suitable manner for maintaining a predetermined, desired position.

Using, in accordance with the present invention, corrugations or other depressions on the belt 2 for establishing whether or not the belt 2 is covered by a product layer immediately below a photodetector 24 is a simple, reliable and advantageous method, but the position of the spreading front 26 and the size of the angle of spreading A can also be determined in other ways. Instead of several stationary photodetectors, it is possible to use e.g. a single movable photodetector for determining the position of the spreading front 26.

It should further be pointed out that the invention is also applicable to an apparatus which, as opposed to that described above, has several spreaders 22 across the width of the belt 2.

Finally, it should be pointed out that although the invention has been described above in connection with a freezer, it is usable in any apparatus of the type which is stated in the introduction to the specification and in which a liquid food product is brought beyond a solidifying temperature or point for conversion into solid phase.

What we claim and desire to secure by Letters Patent is:

1. Method for controlling the flow of a pumpable food product into an apparatus comprising a substantially horizontal belt conveyor having a conveyor belt for converting into a solid state a web or mat of said pumpable food product which is applied from a nozzle to a belt and spreads across the entire width thereof, wherein the angle of the spreading from the location of the nozzle of the food product on the conveyor belt is sensed and compared with a predetermined angle of spreading, and wherein said flow of said pumpable food product is so controlled that the difference between said two angles is reduced.

2. Method as claimed in claim 1, wherein the flow from the nozzle is controlled by stepwise adjustment thereof.

3. A method of controlling the flow of a pumpable food product onto a moving conveyor belt whereupon said food product is frozen into solid form, comprising:
   discharging said pumpable food product onto the belt at approximately the center thereof while simultaneously moving said belt relative to the location of such discharging;
   permitting said pumpable food product to spread across the entire width of said moving belt;
   sensing the position of a spreading front of the pumpable food product as it spreads across the width of said belt and as said belt moves away from the location of said discharging; and
   controlling the rate of discharging based on the sensed location of the spreading front of the pumpable food product on the moving belt.

* * * * *